(12) United States Patent
Back et al.

(10) Patent No.: US 10,035,746 B2
(45) Date of Patent: Jul. 31, 2018

(54) PROCESS FOR THE DECARBOXYLATIVE KETONIZATION OF FATTY ACIDS OR FATTY ACID DERIVATIVES

(71) Applicant: RHODIA OPERATIONS, Paris (FR)

(72) Inventors: Olivier Back, Lyons (FR); Rémy Leroy, Vaulx en Velin (FR); Philippe Marion, Vernaison (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 15/571,979

(22) PCT Filed: May 4, 2016

(86) PCT No.: PCT/EP2016/060106
§ 371 (c)(1),
(2) Date: Nov. 6, 2017

(87) PCT Pub. No.: WO2016/177842
PCT Pub. Date: Nov. 10, 2016

(65) Prior Publication Data
US 2018/0093936 A1    Apr. 5, 2018

(30) Foreign Application Priority Data

May 7, 2015    (EP) .................................... 15305709

(51) Int. Cl.
| C07C 45/48 | (2006.01) |
| C07C 1/24 | (2006.01) |
| C07C 29/00 | (2006.01) |
| C07C 29/145 | (2006.01) |

(52) U.S. Cl.
CPC ............. *C07C 45/48* (2013.01); *C07C 1/24* (2013.01); *C07C 29/145* (2013.01); *C07C 2521/04* (2013.01)

(58) Field of Classification Search
CPC .......... C07C 45/48; C07C 1/24; C07C 29/145
See application file for complete search history.

(56) References Cited

U.S. PATENT DOCUMENTS

| 2,108,133 A | 2/1938 | McCall |
| 4,183,867 A | 1/1980 | Sekiguchi et al. |
| 4,248,793 A | 2/1981 | Sekiguchi et al. |
| 2007/0100166 A1 | 5/2007 | Beavers et al. |
| 2010/0282467 A1 | 11/2010 | Hutchison et al. |
| 2013/0079261 A1 | 3/2013 | Hutchison et al. |
| 2013/0199788 A1 | 8/2013 | Barnes et al. |
| 2014/0336409 A1 | 11/2014 | Barnes et al. |

FOREIGN PATENT DOCUMENTS

| DE | 259191 C | 4/1913 |
| DE | 295657 C | 12/1916 |
| EP | 0351928 A1 | 1/1990 |
| EP | 2468708 A1 | 6/2012 |
| JP | 60032759 A2 | 2/1985 |
| WO | 2007038371 A1 | 4/2007 |
| WO | 2013131766 A1 | 9/2013 |
| WO | 2013167646 A1 | 11/2013 |
| WO | 2013186305 A1 | 12/2013 |

OTHER PUBLICATIONS

Srimani, Dipankar et al.,"Direct Catalytic Olefination of Alcohols with Sulfones", Angewandte Chemie-International Edition (2014) vol. 53 Issue: 41 pp. 11092-11095, (Published: Oct. 6, 2014).
Bolder, Fha et al., "Dehydration of alcohols in the presence of carbonyl compounds and carboxylic acids in a Fischer-Tropsch hydrocarbons matrix", Applied Catalysis A-General (2006) vol. 300 Issue: 1 pp. 36-40, (Published: Jan. 20, 2006).
Vaan Der Klis, F. et al., "Oxidative decarboxylation of unsaturated fatty acids", European Journal of Lipid Science and Technology (2011) vol. 113 Issue: 5 pp. 562-571, (Published: May 2011).
L.W. Holleman et al. "On the formation of higher aliphatic ketones in the thermal decomposition of fat", Rec. Trav. Chim. Pays-Bas, vol. 58, No. 8, 1939, pp. 666-674.

*Primary Examiner* — Sikarl A Witherspoon

(57) ABSTRACT

A process for the decarboxylative ketonization of fatty acids, fatty acid derivatives or mixtures thereof in the liquid phase with metal compounds as catalyst wherein the fatty acids, fatty acid derivatives or mixtures thereof are added sequentially.

20 Claims, No Drawings

PROCESS FOR THE DECARBOXYLATIVE KETONIZATION OF FATTY ACIDS OR FATTY ACID DERIVATIVES

This application is a U.S. national stage entry under 35 U.S.C. § 371 of International Application No. PCT/EP2016/060106 filed May 4, 2016, which claims priority to European application No. 15305709.6 filed on May 7, 2015. The entire contents of these application are explicitly incorporated herein by this reference.

The present invention relates to a process for the manufacture of long chain internal ketones through decarboxylative ketonization of fatty acids or derivatives of fatty acids.

The conversion of acids into respective ketones by decarboxylative ketonization is a well known process which is also commercially used.

The process can be carried out in the gas phase at temperatures usually exceeding 350° C. and usually above 400° C. for fatty acids in the presence of catalytic amounts of metal oxide compounds (e.g. MgO, $ZrO_2$, $Al_2O_3$, $CeO_2$, $MnO_2$, $TiO_2$).

Carrying out the reaction in the gas phase with fatty acids with a high boiling point is difficult as the evaporation of the reactants needs very high temperatures which is detrimental for the selectivity of the process and leads to the formation of undesired by-products.

Carrying out the process in the liquid phase offers certain advantages over the reaction in the gas phase, e.g. usually higher productivities, reduced manufacturing costs and better selectivities which is important for the subsequent work-up of the reaction mixture.

German patent DE 295 657 relates to a process for the manufacture of ketones where monocarboxylic acids having a boiling point exceeding 300° C. are heated in the liquid phase with small amounts of catalytically active metal compounds, silica gels or silicates to temperatures not substantially exceeding 300° C. The organic acid is mixed with the catalytically active species and subsequently heated to the desired reaction temperature. The process is reported to yield the desired ketones in good yield and purity.

The process described in DE 295 657 does not lead to the desired ketones in good yields, however, if the fatty acid starting material comprises fatty acids or fatty acid derivatives having a boiling point of less than 300° C. (which is the case for linear fatty acids having 12 carbon atoms or less such as: lauric acid, capric acid, caprylic acid . . . ) in a more than insignificant amount.

German patent DE 259 191 relates to a process for the manufacture of ketones by heating higher fatty acids with finely distributed metals and lowering the temperature before the ketone starts to decompose. In the example stearic acid is heated with cast iron powder to a temperature of 360° C. and kept at 360° C. for about 4 h and thereafter the product is cooled down and the ketone formed is isolated. The amount of cast iron is 10 wt % based on the amount of stearic acid which corresponds to stoechiometric amounts. Again, the process as described in this reference only yields to low amounts of ketones if fatty acids having 12 carbon atoms or less are used as starting material or are present in the starting material in more than insignificant amounts.

EP2468708 relates to the decarboxylative cross-ketonization of mixtures of aryl- and alkylcarboxylic acids uring iron catalysts such as magnetite nanopowders to obtain alkylarylketones. According to the process claimed a blend of an aromatic monocarboxylic acid, a second monocarboxylic acid selected from benzylic or aliphatic monocarboxylic acids and an iron containing catalyst are heated in a non-aqueous solvent to a temperature of at least 220° C. for at least 10 h with continuous removal of water and carbon dioxide. After termination of the reaction, the blend formed is distilled under reduced pressure and the reaction product is obtained in the distillate. The use of a non-aqueous solvent is considered to be essential. The reaction times of more than 10 hours, however, are not suitable for a synthesis in an industrial scale.

In the PhD thesis of Christoph Oppel ("New methods of ketone synthesis, University of Kaiserslautern 2012), one of the inventors of the aforementioned EP 2468708, experiments for the ketonization of lauric acid with metallic mediators are described. The reaction is carried out at 340° C. with various metal compounds, including Fe and MgO and the ketone 12-tricosanone is obtained in good yields. The reaction is carried out in closed vessels saturated with nitrogen. The water and carbon dioxide formed lead to a build-up of pressure inside the closed system, and the reaction temperature of 340° C. also contributes to the build up of pressure as lauric acid at these temperatures is gaseous. Application of such a process in an industrial scale would necessitate the use of autoclaves which is expensive. The amount of metallic mediator in the examples given in the table on page 88 of the PhD thesis is 50 mol % based on the total amount of acid which corresponds to stoechiometric ratios and the entire amount of the reactants is put together initially and heated up together.

While the processes described in the prior art and referred to above yield ketones in good yields, some of them are not efficient when starting from fatty acids containing 12 atom carbons or less or mixture of fatty acids containing a significant amount of fatty acids having 12 atom carbon or less. Moreover for some of the above mentioned processes, their use in an industrial scale is hampered by problems and necessitate expensive apparatus. Thus there still exists a need for a commercially applicable process for the manufacture of ketones from fatty acids or their derivatives.

It was thus an object of the present invention to develop a facile and easy to use process for the synthesis of ketones by decarboxylative ketonization of fatty acids or fatty acid derivatives in the liquid phase in an open reaction system, especially starting from fatty acids with 12 carbon atoms or less or mixtures of fatty acids comprising at least 10 mol %, based on the entire amount of carboxylic acids, of fatty acids with 12 carbon atoms or less or their derivatives.

This object has been achieved with the process in accordance with claim 1, that is to say a process for the decarboxylative ketonization of fatty acids, fatty acid derivatives or mixtures thereof in the liquid phase with metal compounds as catalyst, characterized in that a) in a first step, elementary metal or a metal compound and the fatty acid, fatty acid derivative or mixture thereof comprising at least 10 mol %, based on the entire amount of fatty acids or fatty acid derivatives, of fatty acids having 12 carbon atoms or less or derivatives of fatty acids having 12 carbon atoms or less, are mixed in a molar ratio of from 1:0.8 to 1:3.5 (molar ratio metal: carboxyl group equivalent) and reacted for a period $P_1$ of from 5 min to 24 h at a temperature $T_1$ of from 100° C. to 270° C. in the substantial absence of added solvents, and b) thereafter the temperature is raised to a temperature $T_2$ which is strictly above 270° C. and up to 400° C., and additional fatty acids, fatty acid derivatives or a mixture thereof comprising at least 10 mol %, based on the entire amount of fatty acids or fatty acid derivatives, of fatty acids having 12 carbon atoms or less or derivatives of such fatty acids, is added over a period of time $P_2$ of from 5 min to 24 h in the substantial absence of added solvents until the molar ratio of fatty acid, fatty acid derivatives or mixtures thereof to metal is in the range of from 6:1 to 99:1.

Certain preferred embodiments of the process in accordance with the present invention are set forth in the dependent claims.

For example, an embodiment set forth in claim 4 (hereinafter, embodiment E*) is directed to a process for the decarboxylative ketonization of fatty acids, fatty acid derivatives or mixtures thereof in the liquid phase with metal compounds as catalyst, characterized in that a) in a first step, elementary metal or a metal compound and the fatty acid, fatty acid derivative or mixture thereof comprising at least 10 mol %, based on the entire amount of fatty acids or fatty acid derivatives, of fatty acids having 12 carbon atoms or less or derivatives of fatty acids having 12 carbon atoms or less, are mixed in a molar ratio of from 1:0.8 to 1:3.5 (molar ratio metal: carboxyl group equivalent) and reacted for a period of from 5 to 240 min at a temperature of from 180 to 270° C. in the substantial absence of added solvents, and b) thereafter the temperature is raised to 280 to 320° C. and additional fatty acids, fatty acid derivatives or a mixture thereof comprising at least 10 mol %, based on the entire amount of fatty acids or fatty acid derivatives, of fatty acids having 12 carbon atoms or less or derivatives of such fatty acids, is added over a period of time of from 1 h to 24 h in the substantial absence of added solvents until the molar ratio of fatty acid, fatty acid derivatives or mixtures thereof to metal is in the range of from 6:1 to 99:1.

Other embodiments of the process in accordance with the present invention are also set forth in the detailed description hereinafter.

Temperature $T_1$

Temperature $T_1$ is of from 100° C. to 270° C.

Temperature $T_1$ is preferably of at least 180° C., more preferably of at least 210° C. and still more preferably of at least 230° C.

Besides, temperature $T_1$ may be of at most 260° C.

Temperature $T_1$ may be from 180° C. to 270° C. or from 210° C. to 260° C. Good results were obtained when $T_1$ ranged from 230° C. to 270° C., in particular from 240° C. to 260° C.

Temperature $T_2$

Temperature $T_2$ is strictly above 270° C. and up to 400° C.

Temperature $T_2$ may be strictly below 280° C. However, it is preferably of at least 280° C., more preferably of at least 290° C. and still more preferably of at least 300° C. It may be strictly above 320° C.

Temperature $T_2$ may be strictly above 360° C. However, it is generally of at most 360° C. and often of at most 340° C. It may be of at most 320° C.

Temperature $T_2$ may be from 280° C. to 320° C. Temperature $T_2$ may also be strictly above 320° C. and up to 360° C.

Good results were obtained when $T_2$ ranged from 280° C. to 360° C., in particular from 300° C. to 340° C.

Difference of temperature $T_2$ minus $T_1$ ($T_2-T_1$)

Difference of temperature $T_2$ minus $T_1$ is advantageously of at least 3° C. It is preferably of at least 10° C., more preferably of at least 30° C. and still more preferably of at least 45° C.

Besides, $T_2-T_1$ is advantageously of at most 100° C. It may be of at most at most 85° C., at most 70° C. or at most 55° C.

Good results were obtained when $T_2-T_1$ ranged from 30° C. to 100° C., in particular from 45° C. to 85° C.

Certain combinations of temperature $T_1$ and of temperature $T_2$

In a first embodiment, $T_1$ is from 230° C. to 270° C., while $T_2$ is from 280° C. to 400° C., preferably from 290° C. to 360° C. and more preferably from 300° C. to 340° C.

In a second embodiment, $T_2$ is strictly below 280° C., while $T_1$ is from 180° C. to 270° C., preferably from 230° C. to 270° C. and more preferably from 240° C. to 260° C.

In a third embodiment, $T_2$ is from 280° C. to 320° C., while $T_1$ is from 180° C. to 270° C., preferably from 230° C. to 270° C. and more preferably from 240° C. to 260° C.

In a fourth embodiment, $T_2$ is strictly above 320° C. and up to 360° C., while $T_1$ is from 180° C. to 270° C., preferably from 230° C. to 270° C. and more preferably from 240° C. to 260° C.

In a fifth embodiment, $T_2$ is strictly above 360° C., while $T_1$ is from 180° C. to 270° C., preferably from 230° C. to 270° C. and more preferably from 240° C. to 260° C.

Period of time $P_1$

Period of time $P_1$ may vary to a large extent depending notably on the nature of the elementary metal or metal compound. In any case, period of time $P_1$ is from 5 min to 24 h.

Period of time $P_1$ is preferably of at least 10 min and more preferably of at least 20 min.

Besides, period of time $P_1$ is preferably of at most 12 h, more preferably of at most 8 h and still more preferably at most 5 h.

Good results were obtained with period of time $P_1$ of from 10 min to 8 h, in particular of from 20 min to 5 h.

Each specified lower limit, upper limit or range for period of time $P_1$ must be considered as explicitly described in combination with each specified lower limit, upper limit or range previously specified for temperature $T_1$.

Period of time $P_2$

Period of time $P_2$ may also vary to a large extent depending notably on the overall amount of acid or acid derivative used. In any case, period of time $P_2$ is from 5 min to 24 h.

Period of time $P_2$ is preferably of at least 30 min, more preferably of at least 1 h and still more preferably of at least 2 h.

Besides, period of time $P_2$ is preferably of at most 16 h and more preferably of at most 8 h.

Good results were obtained with period of time $P_2$ of from 1 h to 16 h, in particular of from 2 h to 8 h.

Each specified lower limit, upper limit or range for period of time $P_2$ must be considered as explicitly described in combination with each specified lower limit, upper limit or range for temperature $T_2$.

First Step

In the first step of the process according to the present invention, elementary metal (or a mixture of elementary metals) or a metal compound (or a mixture of metal compounds) and the fatty acid, fatty acid derivative or mixture thereof comprising at least 10 mol %, based on the entire amount of fatty acids or fatty acid derivatives, of fatty acids having 12 carbon atoms or less or derivatives of such fatty acids, are mixed in a molar ratio of from 1:1.0 to 1:3.0 (molar ratio metal: carboxylate group equivalent) and reacted for a period of time $P_1$ at a temperature $T_1$ in the substantial absence of added solvents, preferably in the absence of solvent.

For example, in embodiment E*, in the first step of the process, elementary metal (or a mixture of elementary metals) or a metal compound (or a mixture of metal compounds) and the fatty acid, fatty acid derivative or mixture thereof comprising at least 10 mol %, based on the entire amount of fatty acids or fatty acid derivatives, of fatty acids having 12 carbon atoms or less or derivatives of such fatty acids, are mixed in a molar ratio of from 1:1.0 to 1:3.0 (molar ratio metal: carboxylate group equivalent) and reacted for a period of time of from 5 to 240 min, preferably of from 10 to 180 min and even more preferably of from 15 to 120 min, at a temperature of from 180 to 270° C., preferably of from 190 to 260° C. and even more preferably of from 210 to 260° C. in the substantial absence of added solvents, preferably in the absence of solvent. In this embodiment E*, reaction times of from 15 to 60 minutes at a reaction temperature of from 220 to 260° C. have sometimes shown to be advantageous.

The number of carbon atoms always refers to the respective number in the free acid; if derivatives are used, the carbon number may be higher.

Suitable metals for use in the process in accordance with the present invention are selected from the group consisting of Mg, Ca, Al, Ga, In, Ge, Sn, Pb, As, Sb, Bi, Cd and transition metals having an atomic number of from 21 to 30. Suitable metal compounds are oxides of the aforementioned metals, naphthenate salts of the aforementioned metals or acetate salts of the aformentioned metals. Magnesium and iron and their oxides, and in particular iron powder, are preferred.

The term fatty acids refers to carboxylic acids containing at least 4 carbon atoms. The term fatty acids derivative refers to anhydrides made by the condensation of 2 fatty acids or to esters made by the condensation of fatty acids with alcohols.

Suitable fatty acid derivatives are esters and anhydrides of fatty acids, but the use of the free fatty acids as such is generally preferred. The esters or anhydrides in the course of the reaction are converted to the acids which then react with the metal or the metal compound. Especially in case of esters, however, alcohols are formed as a by-product which then has to be removed at a later point in time, which requires additional work and costs. However, if esters are derived from lower alcohols such as methanol, ethanol, propanol or butanol, the alcohols are removed progressively over the course of the reaction thanks to a reactive distillation.

The fatty acid or fatty acid derivatives can be used in the form of so called fatty acid or fatty acid derivatives cuts which may be obtained by the hydrolysis or alcoholysis of different natural fats and oils. Accordingly these cuts may contain various amounts of different linear fatty acids or linear fatty acid derivatives with different chain lengths. Just by way of examples fatty acid cuts obtained from coconut oil and comprising mainly $C_{12}$-$C_{18}$ fatty acids may be mentioned here. The skilled person is well aware of other fatty acid cuts obtainable form various sources and will select the best suitable starting materials based on the desired ketones.

Fatty acids having 12 carbon atoms or less, preferably of from 8 to 12 carbon atoms or derivatives of such acids (esters or anhydrides) constitute at least 10 mol % and preferably at least 15 mol % of the entire molar amount of the fatty acid mixture or fatty acids derivatives mixture used as starting material. These acids lead to ketones having a total carbon number of 23 or less which have proved to be advantageous in a number of applications. There is no specific upper limit for the amount of these fatty acids or fatty acid derivatives of acids having 12 carbon atoms or less, i.e. the starting material may also entirely consist of such fatty acids or fatty acid derivatives.

Subject to the above, preferred fatty acids for use in the process of the present invention are hexanoic acid, isostearic acid, caprylic acid, capric acid, lauric acid, myristic acid, palmitic acid, stearic acid, arachidic acid, behenic acid, lignoceric acid, cerotic acid or mixtures thereof and preferred fatty acid derivatives are the esters and anhydrides of these acids.

It is understood that, when one and only one fatty acid or fatty acid derivative is used as the starting material, it must have 12 carbon atoms or less.

The fatty acids may comprise one or more double bonds in the chain such as oleic acid, linoleic acid, linolenic acid, erucic acid, palmitoleic acid or mixtures thereof.

When starting from a single fatty acid, a symmetrical ketone is obtained as the reaction product; when starting from a cut of fatty acids as described above all the ketones formed by the combination of the different alkyl groups of the starting acids are obtained and the distribution of the different mixed ketones generally follows a statistical binomial law. The reaction equation can be summarized as follows:

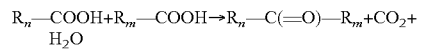

wherein $R_n$ and $R_m$ represent the alkyl groups of the fatty acids present in the cut. It is well apparent that e.g. if three different acids are present, a total of six different ketones may be formed; three symmetrical ketones wherein $R_n$ and $R_m$ are identical and three mixed ketones with different groups $R_n$ and $R_m$.

In accordance with a preferred embodiment the metal is iron powder or the metal compound is iron (II) oxide or a mixed oxide of iron (II) and iron (III) such as e.g. magnetite. Iron powder has economical advantages as it is cheap and abundantly available.

During the first step of the process in accordance with the present invention a metal carboxylate is formed as an intermediate species which in the subsequent step decomposes into the desired ketone and a metal oxide which is the active catalytic species for the subsequent conversion of the acid or acid derivative added sequentially or continuously in the second step to the desired ketone containing mixture.

If a metal is used in the first step, said metal reacts with the fatty acid to a carboxylate of the metal with simultaneous formation of hydrogen gas. If a metal oxide is used in the first step, the formation of the carboxylate is accompanied by the simultaneous formation of water. The overall equation for the carboxylate formation in the first step (for a metal having a valency of 2 as example) can be represented as follows:

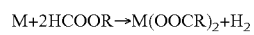

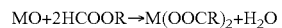

The molar ratio of metal or metal compound to the total amount of carboxylic groups in the starting material in the first step is in the range of from 1:0.8 to 1:3.5 and it is generally preferred to use a molar ratio which is sufficient to form the respective metal carboxylate and to convert all the acid or acid derivative present to the metal carboxylate, i.e. basically leaving no free carboxylic groups after formation of the carboxylate after the first step. Thus, for a bivalent metal, the molar ratio of metal to carboxylic groups is preferably about 1:2 as two equivalents of acid groups are needed to form the metal dicarboxylate of a bivalent metal. If metal oxide compounds are used instead of elementary metal, the molar ratio referred to above is calculated with the amount of elementary metal in the oxide compound. The molar amount of carboxylic groups is calculated taking into account the number of such groups in the fatty acid or fatty acid derivative which is used as a starting material. Thus, for example an anhydride of an acid comprises two carboxylate functionalities and can provide two carboxylic groups for the formation of the metal carboxylate.

The formation of the metal carboxylate in the first step can be conveniently monitored by in situ IR analysis. The carbonyl absorption band of the acid is subject to a bathochromic shift in the metal carboxylate which allows the monitoring of the reaction progress.

In accordance with a particularly preferred embodiment of the process in accordance with the present invention, iron powder is used as metal as same is cheap and abundantly available.

Second Step

In the second step of the process in accordance with the present invention, the temperature is raised to temperature $T_2$ at which temperature the metal carboxylate decomposes advantageously to the desired ketone, metal oxide and carbon dioxide.

For example, in embodiment E*, in the second step of the process, the temperature is raised to 280 to 320° C. at which temperature the metal carboxylate decomposes advantageously to the desired ketone, metal oxide and carbon dioxide.

Additional fatty acids, fatty acid derivatives or a mixture thereof comprising at least 10 mol %, based on the entire amount of fatty acids or fatty acid derivatives, of fatty acids having 12 carbon atoms or less or derivatives of such fatty acids are added in the second step, in the substantial absence of added solvent, preferably in the absence of added solvent. They may be added sequentially or continuously and they are profitably added at a rate avoiding the build-up of substantial amounts of free acid in the reaction system. Again, the progress of the reaction and the conversion of the starting materials to the carboxylates as intermediates and the ketones as final products may be conveniently monitored through appropriate methods like IR analysis.

During the second step, additional fatty acids, fatty acid derivatives or a mixture thereof is added over a period of time $P_2$ which depends notably on the overall amount of acid or acid derivative used.

For example, in embodiment E*, period of time $P_2$ is in the range of from 1 h to 24 h, preferably of from 2 h to 12 h and particularly preferably of from 2 to 8 hours.

The total amount of fatty acid material (fatty acid or fatty acid derivatives) added in the second step of the reaction is such that the overall molar ratio of metal to the amount of carboxylic groups reached at the end of the second step is in the range of from 1:6 to 1:99, i.e. the amount of metal compound is about 1 mol % to about 14 mol % and preferably of from 2 to about 10 mol % of the entire amount of fatty acids or fatty acid derivatives, i.e. the metal or metal compound truly functions in a catalytic manner and is not used up in the course of the reaction. For most of the processes described in the prior art in the liquid phase the metal or metal compound has been used in amounts of more than 50 mol % and in many cases even exceeding equimolar amounts. Such high amounts of metal are not necessary in the process in accordance with the present invention which is a technical as well as an economical advantage of the process in accordance with the present invention over the prior art.

In accordance with the present invention, temperature $T_2$ is strictly above 270° C. and up to 400° C. In accordance of embodiment E* of the present invention, the temperature in the second reaction step is within the range of from 280 to 320° C. and preferably in the range of from 285 to 310° C.

What has been said above for the composition of the starting fatty acid material in the first step of the process in accordance with the present invention also applies to the second step.

The process in accordance with the present invention is carried out in an unpressurized system, i.e. without applying superatmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

The process in accordance with the present invention is carried out in the substantial absence of added solvent. The desired ketone formed during the reaction basically acts as a solvent for the reaction. Since the ketone formed generally as a higher boiling point than the fatty acids or fatty acid derivatives used as a starting material, this allows to carry out the reaction in the liquid phase as desired without the addition of an external solvent which would have to be removed at the end of the reaction and which is cost and labour intensive and thus undesirable.

Period of Time $P_{12}$

The additional fatty acids, fatty acid derivatives or mixture thereof may be added over period of time $P_2$ under the above specified conditions immediately after the temperature has been raised to $T_2$ (which particular embodiment corresponds to $P_{12}$, as defined hereinafter, equal to 0).

Alternatively, after the temperature has been raised to $T_2$ and before the additional fatty acids, fatty acid derivatives or mixture thereof is added over period of time $P_2$, said temperature may be maintained at temperature $T_2$ during a period of time $P_{12}$ (>0).

Period of time $P_{12}$ is preferably of at least 30 min and more preferably of at least 1 h.

Besides, period of time $P_{12}$ is preferably of at most 5 h and more preferably of at most 3 h.

Good results were notably obtained with P12 ranging from 30 min to 300 min, especially from 1 h to 3 h.

Period of Time $P_{23}$

Immediately after the additional fatty acids, fatty acid derivatives or mixture thereof has been added over period of time $P_2$, the temperature may be decreased, possibly down to a temperature $T_3$ which is preferably in the range of from about 5° C. to about 50° C. (which particular embodiment corresponds to $P_{23}$, as defined hereinafter, equal to 0). Temperature $T_3$ may be the room temperature or a temperature slightly above the room temperature.

Alternatively, after the additional fatty acids, fatty acid derivatives or mixture thereof has been added over period of time $P_2$, the temperature may be maintained at temperature $T_2$ during a period of time $P_{23}$ (>0).

Period of time $P_{23}$ is preferably of at least 30 min and more preferably of at least 1 h.

Besides, period of time $P_{23}$ is preferably of at most 5 h and more preferably of at most 3 h.

Good results were notably obtained when $P_{23}$ ranged from 30 min to 300 min, especially from 1 h to 3 h.

Recovery of the Fatty Acid Ketone and Recycling of Metallic Compounds

Once the fatty acid derivative or fatty acid added in the second step of the process in accordance with the present invention has been converted, the desired ketone can be easily obtained e.g. by distillation at reduced pressure. One can take also advantage of the ferromagnetic properties of the metallic compounds formed during the reaction (such as iron oxides) to separate the metallic compounds from the ketone by applying a magnetic field. Another way to separate the products ketone from the metal compounds is through a simple filtration as the metallic compounds are not soluble in the ketones obtained as reaction product. The skilled person is aware of representative techniques so that no further details need to be given here.

The entire process can be advantageously carried out under inert gas atmosphere and suitable inert gases are e.g. nitrogen or argon, to name only two examples.

In accordance with another preferred embodiment of the present invention, after separation of the desired ketone, the remaining residue constituted mainly of metallic compounds (for example the bottom material after distillation) can be directly reused for a second cycle of addition of fatty acid or fatty acid derivative to be converted to the desired fatty acid ketones. Overall, amounts of as low as one mole percent of metal or metal compound, relative to the amount of carboxylic acid equivalents is sufficient to obtain the desired ketones in good yield. It has been found, that up to four cycles are possible without a significant loss of catalytic activity of the metal or metal compound (cf. Example 1).

Accordingly, in another preferred embodiment of the process of the present invention, at the end of step b) the metallic compounds are separated from the products using conventional techniques and then are recycled for the conversion of another batch of fatty acids or fatty acids derivatives or a mixture thereof comprising at least 10 mol %, based on the entire amount of fatty acids or fatty acid derivatives, of fatty acids having 12 carbon atoms or less or derivatives of such fatty acids.

The yield of the desired ketones after step two normally exceeds 60 present, more preferably 70% and can be as high as more than 90%.

Use of the Fatty Acid Ketone for the Synthesis of Secondary Fatty Alcohols

The fatty acid ketones obtained in accordance with the process of the present invention are advantageously used for the manufacture of respective secondary fatty alcohols. To obtain these alcohols the fatty acid ketones obtained in the process in accordance with the present invention are subjected to a hydrogenation reaction. The reaction is usually carried out using heterogeneous transition metal catalysts on a support in an autoclave with hydrogen gas as hydrogenating agent.

Just by way of example palladium catalysts supported on carbon materials may be mentioned as catalysts. The hydrogenation reaction is usually carried out at a hydrogen pressure of from 500 to 5000 kPa and at a temperature in the range of from 120 to 200° C. without the use of an added solvent.

Use of the Secondary Fatty Alcohols for the Synthesis of Internal Olefins

The secondary alcohols obtained as described above may be further converted to internal olefins by a dehydration reaction.

Preferably, the dehydration is carried out in the substantial absence of an added solvent, preferably in the absence of added solvent, using aluminum oxide, preferably $\eta$-$Al_2O_3$ as catalyst at a temperature in the range of from 250 to 350° C. and for a time of 30 min to 6 h.

The internal olefins obtained after the dehydration as described above show a very low degree of isomerization of the double bond. The double bond is formed next to the alcohol group which is removed and so the olefins are internal olefins having the double bond mainly in the middle of the chain. It is apparent that the structure of the olefin obtained is mainly determined by the structure of the starting alcohols. The dehydration reaction is usually carried out in an inert atmosphere.

Sulfonation of the Internal Olefins

The internal olefins obtained after the dehydration described above can be sulfonated followed by an alkaline hydrolysis to obtain internal olefin sulfonates which are useful as surfactants.

According to a first alternative, the sulfonation can be carried out using a falling film reactor, possibly a lab scale film reactor. This reactor may be equipped with a cooling jacket supplied with cold water in order to prevent temperature increases in the reactor due to the high exothermicity of the reaction. For this reaction, the temperature of the cooling jacket is usually set-up at around 0° to 8° C.

A gas flow consisting of a mixture of sulfonating agent (e.g. anhydrous $SO_3$) diluted with carefully dried inert gas (e.g. nitrogen or air) at a concentration usually in the range of from 0.5 to 10, preferably of from 1 to 5% v/v (particularly preferred around 2.5% v/v) is contacted with a falling film of liquid olefins. The flows of gas and liquid phases are set-up in order to ensure a residence time of from 10 seconds to 10 min, preferably of from 1 min to 6 min (e.g. 3 minutes) in the reactor and a mole ratio $SO_3$: Internal olefin in the range of from 0.7:1 to 1.5:1, preferably of from 0.8:1 to 1.2:1 and most preferably of from 0.9:1 to 1.1:1 (e.g. most preferably of 1.05: 1).

When using a mixture of internal olefins with different chain lengths (and thus different molecular weights) the total molar flow of internal olefins can be calculated using the average molecular weight of the mixture of olefins.

Following the sulfonation reaction the mixture exiting the reactor (composed mainly of $\beta$-sultones) can be allowed to age in order to allow trans-sulfonation to occur and to increase the conversion of starting olefins.

Thereafter, the obtained mixture can be neutralized using an aqueous solution of a base (e.g. NaOH) in a reactor which is preferably equipped with a mechanical stirring. Hydrolysis is then carried out by heating the mixture under mechanical stirring. During this stage of the process, the $\beta$-sulfone is transformed into to desired Internal Olefin Sulfonates through a ring opening reaction.

The sulfonation, digestion and hydrolysis reactions can be followed using NMR analysis. At the end of the process the amount of water in the medium may be adjusted in order to reach an aqueous solution of Internal Olefins Sulfonates with a desired concentration of active matter.

According to a $2^{nd}$ embodiment the sulfonation may be carried out in a (batch) reactor equipped with a mechanical stirring in the liquid phase using an in-situ prepared sulfonating reagent, e.g. "$SO_3$-dioxane". This embodiment is now described by way of an example.

In a round bottom flask anhydrous dioxane and anhydrous trichloromethane (mixture ratio 1:2 to 1:5 v/v) are mixed and cooled down to a temperature in the range of from −5 to 10° C., preferably to about 0° C. Then liquid $SO_3$ (2 molar equivalents) is slowly added under stirring during 10 minutes to generate the complex $SO_3$-dioxane which precipitates out from the mixture as white crystals.

The internal olefins (1 equivalent) are then slowly added under stirring at a temperature of from −5 to 10° C., preferably about 0° C., to the reaction medium during a period of from 0.3 to 3 h, preferably during appr. 1 hour and the mixture is allowed to warm up to room temperature. During this time the color of the mixture changes from light yellow to dark brown and NMR analysis indicates that almost full completion of internal olefins has occurred (around 94% of olefin conversion to sultones). All the volatiles ($CHCl_3$ and dioxane) are then removed under vaccum.

Then 2,4 equivalents of an aqueous NaOH solution (10 wt %) are added to the residue and the resulting mixture is stirred at room temperature during appr. 1 hour in order to ensure complete neutralization.

Hydrolysis is then performed by stirring the resulting reaction mixture at 95° C. overnight. NMR analysis indicates full conversion of sultones to internal olefin sulfonates.

At the end of the process the amount of water is adjusted in order to reach an aqueous solution of Internal Olefins Sulfonates with a suitable concentration of active matter, e.g. 30 wt %.

The process of the present invention thus offers an easy access to internal ketones which are versatile starting materials for a variety of products as outlined above.

The process yields the desired ketones in high yield with only minor amounts (if at all) of undesired by-products being obtained and which can be easily separated from the reaction mixture.

The ketones may be separated from the reaction mixture by convenient and economic processes and the catalytic material can be used for several catalytic cycles without significant deterioration of catalytic activity.

The following examples show the effectiveness of the process and further explain the process of the present invention.

EXAMPLE 1

Synthesis of 12-tricosanone (diketone of lauric acid)

The reaction was carried under argon in a round bottom flask equipped with mechanical stirring, Dean Stark apparatus and an addition funnel. In the reactor, 700 mg of iron powder were dispensed and 20g of lauric acid was introduced into the addition funnel.

A first partial amount of 5 g of acid was added into the reactor and the temperature was brought to 250° C. The mixture was stirred at this temperature for 30 minutes during which the color of the media changed to black and $H_2$ gas was released.

Then the temperature was raised to 300° C., the mixture was stirred during 1 h 30 and the remaining amount of lauric acid (15 grams) was slowly added into the reactor during 4 h 30 min at a flow rate which allowed keeping concentration of lauric acid in the reaction media very low (no accumulation of free acid in solution).

At the end of the reaction, the addition funnel was replaced by a distillation apparatus and the products were distilled off at 290° C.-340° C. under 5 kPa pressure.

Then the distillation apparatus was replaced by the addition funnel containing a new batch of 20 g of fatty acids and the operations described above were repeated for another cycle. No additional amount of iron was needed. The residue in the flask remaining after distillation was efficient to convert the next batch of acids.

Overall 4 cycles were carried out without any loss of performances reducing thereby the concentration of iron to less than 1 wt % relative to fatty acids amount converted.

The conversion, selectivity and yield (measured by gas chromatography (GC) and isolated) are given in Table 1 below.

TABLE 1

(all values in % of theory)

| Cycle no. | Conversion | Selectivity | Raw yield | Isolated yield |
|---|---|---|---|---|
| 1 | 100 | 90 | 90 | 77 |
| 2 | 100 | 89 | 89 | 70 |
| 3 | 100 | 87 | 87 | 85 |
| 4 | 100 | 89 | 89 | 87 |

The data show the superior selectivity and yield of the desired ketone.

EXAMPLE 2

Cut of Coco Fatty Acids as Starting Material

Conversion of 400 g of coco fatty acids having the following weight distribution: $C_{12}$: 55%, $C_{14}$: 21%, $C_{16}$: 13%, $C_{18}$: 12%.

The transformation was carried out using 6.4 g of iron powder (1.6 wt %) and through 2 cycles involving a total of 200 g of fatty acids for each cycle.

The reaction was carried under argon in a 1 l round bottom flask equipped with mechanical stirring, Dean-Stark apparatus and an addition funnel.

Into the 250 mL addition funnel 200 g of coco fatty acids were introduced which were maintained in molten form by an external heater.

6.4 g of iron powder were dispensed into the reactor and a first portion of fatty acids (around 58 mL) were added into the reactor. The mixture was stirred (500 rpm) at 250° C. during 30 minutes in order to convert metallic iron to iron salts. During this period, the mixture color changed to black and hydrogen was released. Then the temperature was raised to 300° C.-320° C. to perform the transformation to fatty ketones. The mixture was stirred at this temperature during 1 h 30 and the remaining part of fatty acids was slowly added in the reactor during 5 hours at a flow which allowed keeping a low concentration of fatty acids in solution (no accumulation of free acids in solution). At the end of the reaction, the addition funnel was replaced by a distillation apparatus and the fatty ketones were recovered by distillation (290° C.-340° C., 5 kPa).

A first crop of 141 g of fatty ketone was recovered as a white wax.

The residue left in the reactor flask and mainly constituted of iron salts was used to convert the remaining 200 g of fatty acids in a second cycle. To achieve this, the distillation apparatus was replaced by the addition funnel containing 200 g of molten fatty acids and the operational steps described above were repeated.

The total yield of the reaction after these 2 cycles was: 79% isolated as a white wax.

EXAMPLE 3

Conversion of Internal Ketones to Secondary Alcohols

This example describes the hydrogenation of the ketones obtained in accordance with the present invention to obtain the corresponding secondary fatty acid alcohols. The reaction was carried out without any solvent using heterogeneous Pd/C (3%) as a catalyst and in an autoclave equipped with a Rushton turbine.

The hydrogenation was carried out on a cut of internal fatty ketones obtained by condensation reaction performed on a cut of $C_{12}$-$C_{18}$ coco fatty acids following the procedure described in Example 2.

The reaction was carried out in a 750 mL autoclave equipped with a Rushton turbine. 28 g of Pd/C (3%) and 280 g of fatty ketones were introduced into the reactor which was sealed. Then the temperature was brought to 80° C. and the mixture was stirred at 1000 rpm. The reactor atmosphere was purged 3 times with 4 MPa of nitrogen then 3 times with 3 MPa of hydrogen. The temperature was then raised to 150° C. and the mixture was stirred at this temperature maintaining 3 MPa of hydrogen until completion of the reaction (monitored by GC analysis). At the end of the reaction, the mixture was allowed to cool down to 80° C. and the reactor was purged with nitrogen. A 1st crop of the product (180 g) was obtained through filtration and the remaining part was extracted using 400 mL of hot toluene. After evaporation of the solvent, a total amount of 247 g of white solid was obtained corresponding to an isolated yield of 88%.

EXAMPLE 4

Dehydration of Secondary Alcohols to Internal Olefins

In this example the secondary fatty alcohols obtained in Example 3 were dehydrated with limited isomerization of C=C bond. The reaction was carried out without solvent and using $Al_2O_3$-η as a catalyst. Water generated during the reaction was trapped with a Dean-Stark apparatus.

The olefins obtained were long straight chain internal olefins with C=C double bond localized around the middle of the chain. The structure of the olefin was mainly determined by the structure of the starting alcohols obtained in the $2^{nd}$ step. When starting with a cut of fatty acids not too wide (for example cut of $C_{12}$-$C_{18}$), the obtained ketone and the alcohols obtained by hydrogenation are almost symmetrical with —OH localized nearly in the middle of the chain. Therefore after dehydration the C=C double bond is located close to the middle of the chain.

The reaction was carried out under argon.

47 g of a cut of internal alcohols obtained in accordance with Example 3 followed by 4.7 g of $Al_2O_3$-η were added in a round bottom flask equipped with a Dean-Stark apparatus and magnetic stirring. The mixture was then stirred at 300° C. during 2 hours. After completion of the reaction, the product was extracted using 150mL of hot toluene. After evaporation of the solvent, the product was obtained as pale yellow liquid (39 g) corresponding to an isolated yield of 87%.

The product consisted of a cut of internal fatty olefins with C=C bond localized almost in the middle of the chain. When starting from a cut of coco fatty acids $C_{12}$-$C_{18}$ with even number of carbon atoms, the olefins obtained had an odd number of carbon atoms. The weight distribution of the olefins depending on the weight distribution of the starting fatty acids followed approximately a binomial distribution.

EXAMPLE 5

Comparative Example

Lauric acid was mixed with 12.5 mol % of iron powder and heated to 298° C. (boiling point of lauric acid) and kept at this temperature for 5 hours. Thereafter the composition of the reaction product was determined. The yield of 12-tricosanone was only 18% and a significant amount of undecane was formed (8%). Furthermore, substantial amounts of unreacted lauric acid were still present (total conversion of lauric acid is 46%).

This comparative example shows that adding the entire amount of acid in one step and not sequentially does not yield the desired ketones in a satisfactory yield and in addition a large amount of undesired by-products is formed.

EXAMPLE 6

Synthesis of Nonadecan-10-one (diketone of $C_{10}$ capric acid)

The reaction was carried under argon in a 250 mL round bottom flask equipped with mechanical stirring, Dean-Stark apparatus and an addition funnel. In the reactor, 2.0 g (35.8 mmol) of iron powder were dispensed and 50 g (290.4 mmol) of capric acid were introduced into the addition funnel.

A first partial amount of 12.5 g of capric acid was added into the reactor and the temperature was brought to 250° C. The mixture was stirred at this temperature during 1 h 45. During this time the color of the media changed to black and H2 gas was released. FTIR analysis of the crude mixture showed complete formation of intermediate iron carboxylate.

The temperature was then raised to 315° C. and the mixture was stirred during 1 h 30 in order to transform the iron carboxlyate complex to ketone, $CO_2$ and iron oxide.

The remaining amount of capric acid (37.5 g) was then slowly added into the reactor during 5 h 00 at a flow rate which allowed keeping concentration of capric acid in the reaction media very low (no accumulation of free acid in solution). In practice this could be done by the successive slow additions of fractions of 12.5 g of capric acid every 1.5 h.

After the addition of capric acid was completed, the mixture was allowed to stir at 315° C. until the intermediate iron complex was not detected anymore by FTIR.

When the reaction was completed, the mixture was allowed to cool down at room temperature and 200 mL of $CHCl_3$ were added to the crude media. The mixture was stirred at 40° C. in order to solubilize the product (nonadecan-10-one). The obtained suspension was filtered on a silica plug and eluted using 1.5 L of chloroform. Evaporation of the solvent afforded 39.7 g (140.5 mmol) of the product nonadecan-10-one as an analytically pure yellow powder (97% isolated yield).

EXAMPLE 7

Synthesis of a $C_{15}$-$C_{35}$ Ketones Cut Starting from a $C_8$-$C_{18}$ Coco Saturated Fatty Acids Cut The reaction was carried under argon in a 750 mL reactor equipped with mechanical stirring, Dean-Stark apparatus and an addition funnel. In the reactor, 6.8 g (0.12 mol) of iron powder were dispensed and 200 g (0.97 mol) of the coco saturated fatty acids cut (with the following distribution: $C_8$: 7 wt %, $C_{10}$: 8 wt %, $C_{12}$: 48 wt %, $C_{14}$: 17 wt %, $C_{16}$: 10 wt %, $C_{18}$: 10 wt %) were introduced into the addition funnel.

A first partial amount of 50 g of fatty acids was added into the reactor and the temperature was brought to 250° C. The mixture was stirred at this temperature during 4 h 00. During this time the color of the media changed to black and $H_2$ gas was released. FTIR analysis of the crude mixture showed complete formation of intermediate iron carboxylate complexes.

The temperature was then raised to 330° C. and the mixture was stirred at this temperature during 2 h 00. During this period of time, the intermediate iron carboxylate complexes were decomposed to fatty ketones, iron oxide and $CO_2$.

The remaining fatty acids (150 g) were slowly introduced into the reactor, at a flow rate such that the temperature of the reaction medium did not fall down below 320° C. and which allowed keeping the concentration of fatty acids in the reaction medium very low. An average addition flow rate of around 25 g fatty acids/hour proved to be satisfactory. Practically, this was achieved through the successive slow additions (1 hour per addition) of 3 portions of 50 g of melted fatty acids followed by 1 hour of stirring at 330° C. between each addition.

At the end of the third and last addition, the crude medium was stirred at 330° C. during 2 h and the reaction progress was monitored through FTIR. When the reaction was completed (no more iron complex detected by FTIR), the mixture was allowed to cool down at room temperature and 400 mL of $CHCl_3$ was added to the crude media. The mixture was stirred at 40° C. in order to solubilize the product ($C_{15}$-$C_{35}$ ketones). The obtained suspension was filtered on a silica plug (400 g) and eluted using 3 L of chloroform. Evaporation of the solvent afforded 161 g (0.46 mol) of the product $C_{15}$-$C_{35}$ ketones as an analytically pure white wax (95% isolated yield).

Should the disclosure of any patents, patent applications, and publications which are incorporated herein by reference conflict with the description of the present application to the extent that it may render a term unclear, the present description shall take precedence.

The invention claimed is:

1. A process for the decarboxylative ketonization of fatty acids, fatty acid derivatives or mixtures thereof in the liquid phase with metal compounds as catalyst, wherein
   a) in a first step, elementary metal or a metal compound and the fatty acid, fatty acid derivative or mixture thereof comprising at least 10 mol %, based on the entire amount of fatty acids or fatty acid derivatives, of fatty acids having 12 carbon atoms or less or derivatives of fatty acids having 12 carbon atoms or less, are mixed in a molar ratio of from 1:0.8 to 1:3.5 (molar ratio metal: carboxyl group equivalent) and reacted for a period $P_1$ of from 5 min to 24 h at a temperature $T_1$ of from 100° C. to 270° C. in the substantial absence of added solvents, and
   b) thereafter the temperature is raised to a temperature $T_2$ which is strictly above 270° C. and up to 400° C., and additional fatty acids, fatty acid derivatives or a mixture thereof comprising at least 10 mol %, based on the entire amount of fatty acids or fatty acid derivatives, of fatty acids having 12 carbon atoms or less or derivatives of such fatty acids, is added over a period of time $P_2$ of from 5 min to 24 h in the substantial absence of added solvents until the molar ratio of fatty acid, fatty acid derivatives or mixtures thereof to metal is in the range of from 6:1 to 99:1.

2. The process according to claim 1 wherein temperature $T_1$ is from 230° C. to 270° C.

3. The process according to claim 1 wherein temperature $T_2$ is from 280° C. to 320° C.

4. The process according to claim 3 wherein temperature $T_1$ is from 180° C. to 270° C., period of time $P_i$ is from 5 min to 240 min, and period of time $P_2$ is from 1 h to 24 h.

5. The process according to claim 1 wherein temperature $T_2$ is strictly above 320° C. and up to 360° C.

6. The process in accordance with claim 1 wherein a metal selected from the group consisting of Mg, Ca, Al, Ga, In, Ge, Sn, Pb, As, Sb, Bi, Cd and transition metals having an atomic number of from 21 to 30 or a mixture thereof or an oxide of these metals or a mixture thereof is used.

7. The process in accordance with claim 1 wherein water formed during the reaction is continuously removed from the reaction mixture.

8. The process in accordance with claim 4 wherein step a) is carried out at a temperature $T_1$ of from 190° C. to 260° C. for a duration of from 15 min to 120 min and the fatty acid, fatty acid derivative or mixture thereof in step b) is added over a period $P_2$ of from 2 hours to 12 hours.

9. The process in accordance with claim 1 wherein a fatty acid derivative selected from esters and anhydrides is used as starting material.

10. The process in accordance with claim 1 wherein one and only one fatty acid is used as starting material.

11. The process in accordance with claim 1 wherein a fatty acid cut is used as starting material.

12. The process in accordance with claim 11 wherein the acid cut is a coconut oil fatty acid cut.

13. The process in accordance with claim 1 wherein, after the temperature has been raised to $T_2$ and before the additional fatty acids, fatty acid derivatives or mixture thereof is added over period of time $P_2$, said temperature is maintained at temperature $T_2$ during a period of time $P_{12}$ of from 30 min to 300 min.

14. The process in accordance with claim 1 wherein, after the additional fatty acids, fatty acid derivatives or mixture thereof has been added over period of time $P_2$, the temperature is maintained at temperature $T_2$ during a period of time $P_{23}$ of from 30 min to 300 min.

15. The process in accordance with claim 1 wherein at the end of step b) the metallic compounds are separated from the products using conventional techniques and then are recycled for the conversion of another batch of fatty acids or fatty acids derivatives or a mixture thereof comprising at least 10 mol %, based on the entire amount of fatty acids or fatty acid derivatives, of fatty acids having 12 carbon atoms or less or derivatives of such fatty acids.

16. The process according to claim 4, wherein the temperature $T_1$ is from 210° C. to 260° C.

17. The process in accordance with claim 10 wherein the one and only one fatty acid is capric acid or lauric acid.

18. The process according to claim 1, wherein an internal ketone manufactured through decarboxylative ketonization of the fatty acid, fatty acid derivative or mixture thereof is subjected to a hydrogenation reaction to manufacture a secondary fatty alcohol.

19. The process according to claim 18, wherein the secondary fatty alcohol is further converted to an internal olefin by a dehydration reaction.

20. The method according to claim 19, wherein the internal olefin obtained after the dehydration is sulfonated, followed by an alkaline hydrolysis to obtain an internal olefin sulfonate.

* * * * *